United States Patent [19]
Goto et al.

[11] Patent Number: 6,022,533
[45] Date of Patent: Feb. 8, 2000

[54] TABLETS CONTAINING ANION EXCHANGE RESIN

[75] Inventors: Takeshi Goto; Tatsuya Meno, both of Tsukuba, Japan

[73] Assignee: Hisamitsu Pharmaceutical Co. Inc., Saga-ken, Japan

[21] Appl. No.: 09/000,314

[22] PCT Filed: Aug. 2, 1996

[86] PCT No.: PCT/JP96/02189

§ 371 Date: Jan. 30, 1998

§ 102(e) Date: Jan. 30, 1998

[87] PCT Pub. No.: WO97/04789

PCT Pub. Date: Feb. 13, 1997

[30] Foreign Application Priority Data

Aug. 2, 1995 [JP] Japan .................................. 7-226926

[51] Int. Cl.⁷ .................................................. A61K 31/785
[52] U.S. Cl. .......................................................... 424/78.12
[58] Field of Search ............................... 424/78.1, 78.16, 424/78.12

[56] References Cited

U.S. PATENT DOCUMENTS

| | | | |
|---|---|---|---|
| 4,959,219 | 9/1990 | Chow et al. | 424/78.16 |
| 5,178,854 | 1/1993 | Asami et al. | 424/78.35 |
| 5,372,823 | 12/1994 | Bequette et al. | 424/78.1 |
| 5,665,348 | 9/1997 | Okayama et al. | 424/78.1 |
| 5,709,880 | 1/1998 | Del Corral et al. | 424/78.1 |
| 5,800,809 | 9/1998 | Okayama et al. | 424/78.12 |

*Primary Examiner*—Peter F. Kulkosky
*Attorney, Agent, or Firm*—David G. Conlin; Peter F. Corless; Dike, Bronstein, Roberts & Cushman, LLP

[57] ABSTRACT

The present invention relates to a pharmaceutical composition comprising anion exchange resin, silicon dioxide, crystalline cellulose, and pharmaceutically acceptable carriers and more particularly to tablets containing anion exchange resin prepared by mixing anion exchange resin, silicon dioxide and crystalline cellulose without adding water and tabletting the mixture. More preferably, the present invention relates to said pharmaceutical composition or tablets wherein the anion exchange resin is non-crosslinked anion exchange resin represented by the formula (I):

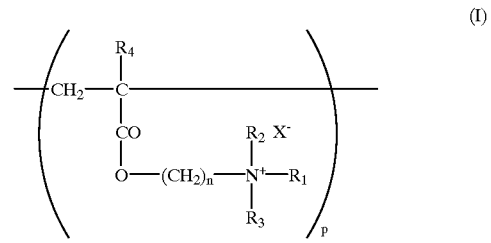

wherein $R_1$ is an aralkyl group having from 7 to 10 carbon atoms or An alkyl group having from 1–20 carbon atoms; $R_2$ and $R_3$ are each independently the same or different and represent a lower alkyl group having from 1–4 carbon atoms; $R_4$ is a hydrogen atom or a lower alkyl group having 1–4 carbon atoms; X is a physiologically acceptable counter ion; n is an integer of from 1 to 3; and p is an average degree of polymerization of from 10 to 10,000.

17 Claims, No Drawings

TABLETS CONTAINING ANION EXCHANGE RESIN

This application has been filed under 37CFR371. The International Application number is PCT/JP96/02189.

TECHNICAL FIELD

The present invention relates to tablets containing anion exchange resin useful as a cholesterol depressant, particularly non-crosslinked anion exchange resin represented by the formula (I):

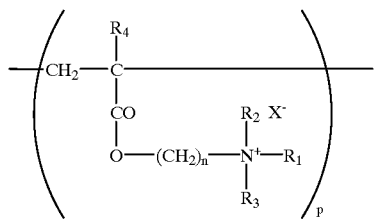

(wherein $R_1$ is an aralkyl group having from 7 to 10 carbon atoms or An alkyl group having from 1 to 20 carbon atoms; $R_2$ and $R_3$ are each independently the same or different and represent a lower alkyl group having from 1 to 4 carbon atoms; $R_4$ is a hydrogen atom or a lower alkyl group having 1–4 carbon atoms; X is a physiologically acceptable counter ion; n is an integer of from 1 to 3; and p is an average degree of polymerization of from 10 to 10,000)
and the invention relates to coating tablets using the same, and more particularly, to coating tablets with excellent stability, in which the content of the active ingredient is increased in order that they can be administered with ease and that the number of the tablets to be administered can be decreased.

In addition, the invention also relates to a method for producing the tablets and coated tablets.

BACKGROUND ART

Cholestyramine of a crosslinked type, which is a conventional cholesterol depressant, is problematic in that its amount to be administered is large (8 to 16 g/day) and that it must be administered in the form of its suspension. Therefore, many studies have heretofore been made to produce tablets and coated tablets of anion exchange resins. For example, a method has been reported of coating tablets of a solid cholestyramine resin having a water content of from 8 to 14% with a melt of polyethylene glycol and stearic acid in the presence of no solvent to give coated tablets, which do not swell in the mouth (see Japanese Patent Application Laid-Open No. 3-236326).

Regarding tablets of an imidazole-type anion exchange resin (see Japanese Patent Application Laid-Open No.60-209523), known are a method of producing those tablets in the presence of a predetermined amount of water (see Japanese Patent Application Laid-Open No. 2-286621); a method of producing coated tablets by coating those tablets as prepared in the presence of a predetermined amount of water, with hydroxypropyl cellulose or the like (see Japanese Patent Application No. 4-320155 (published before examination as Laid-Open No. 6-157325)); and a method of producing those tablets in the presence of a predetermined amount of water and silicon dioxide (see Japanese Patent Application Laid-Open No. 7-97330).

However, the conventional methods require the addition of a predetermined amount of water to the hygroscopic anion exchange resins being tabletted.

The present inventors have already reported that non-crosslinked anion exchange resin represented by the formula (I):

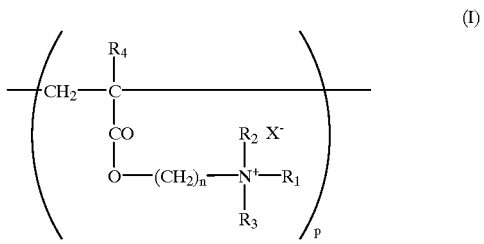

(wherein $R_1$ is an aralkyl group having from 7 to 10 carbon atoms or An alkyl group having from 1 to 20 carbon atoms; $R_2$ and $R_3$ are each independently the same or different and represent a lower alkyl group having from 1 to 4 carbon atoms; $R_4$ is a hydrogen atom or a lower alkyl group having 1–4 carbon atoms; X is a physiologically acceptable counter ion; n is an integer of from 1 to 3; and p is an average degree of polymerization of from 10 to 10,000) is extremely useful as a cholesterol depressant (WO 93/13781). Because this anion exchange resin is a non-crosslinked and linear polymer, it does not expand by swelling unlike cross-linked polymers such as cholestyramine and so on, so there is no side effects such as feeling of distension in the abdomen or constipation accompanying swelling. Further, the effective adsorption of bile acid per unit weight is large, so it is anion exchange resin of extremely high usefulness.

However, this agent is soluble in water and has strong astringency, and in addition, it is highly hygroscopic and deliquescent. Therefore, the novel, non-crosslinked cholesterol depressant comprising the compound of formula (II) is problematic in that, if tabletted in any of the conventional methods that require water in the mixing step, it is formed into tablets with poor strength and stability since its flowability and tablettability is very poor. Even if the cholesterol depressant comprising the compound of formula (II) is tabletted in the absence of water, the resulting tablets are still problematic in that they are very astringent because of the strong astringency intrinsic to the compound of formula (II) itself. The dose of the compound of formula (II), though varying depending on the case to which it is administered, is relatively large or is generally from 0.1 to 9 g/day, preferably from 0.1 to 5 g/day. Tablets comprising the compound of formula (II) and containing a large amount of vehicles in order to reduce the bitterness of the compound are problematic in that the number of the tablets to be administered at a time shall be large.

In order to produce practical medicine products comprising the compound of formula (II) with such extremely high usefulness, it is desired to formulate the compound into highly-stable preparations without strong astringent while adding thereto the smallest possible amount of vehicles as possible.

DISCLOSURE OF THE INVENTION

As a result of further study in view of the above problem, the present inventors found that anion exchange resin, particularly non-crosslinked anion exchange resin represented by the formula (I):

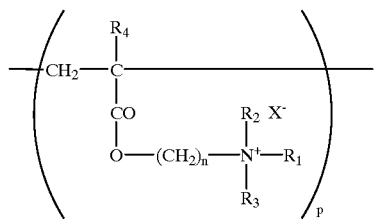

(wherein $R_1$ is an aralkyl group having from 7 to 10 carbon atoms or An alkyl group having from 1–20 carbon atoms; $R_2$ and $R_3$ are each independently the same or different and represent a lower alkyl group having from 1 to 4 carbon atoms; $R_4$ is a hydrogen atom or a lower alkyl group having 1–4 carbon atoms; X is a physiologically acceptable counter ion; n is an integer of from 1 to 3; and p is an average degree of polymerization of from 10 to 10,000) can be industrially prepared tablets by tabletting a mixture without adding water, which comprises that the cholesterol depressant contains non-crosslinked anion exchange resin and that at least silicon dioxide and crystalline cellulose are added into the depressant, and further these tablets are coated as base tablets with a coating agent containing cellulose and so on to solve the above problem.

The present invention relates to a pharmaceutical composition containing anion exchange resin, silicon dioxide, crystalline cellulose and pharmaceutically acceptable carriers. Further, the present invention relates to tablets containing anion exchange resin prepared by adding at least silicon dioxide and crystalline cellulose to the anion exchange resin and tabletting the mixture to which water is not added. Further, the present invention relates to a process for producing tablets containing anion exchange resin which comprises adding at least silicon dioxide and crystalline cellulose to the anion exchange resin and tabletting the mixture without adding water.

More specifically, the present invention relates to tablets containing non-crosslinked anion exchange resin prepared by adding at least silicon dioxide and crystalline cellulose to the compound represented by the formula (I) and tabletting the mixture without adding water. Further, the present invention relates to a process for producing tablets containing non-crosslinked anion exchange resin which comprises adding at least silicon dioxide and crystalline cellulose to the compound represented by the formula (I) and tabletting the mixture to which water is not added.

If one of the components of silicon dioxide and crystalline cellulose lacks, tabletting properties are not only worsened, but tabletting yield is also significantly worsened due to high scattering of tablet weights, cracking on the surfaces of tablets and fracture of the edges thereof (see Comparative Examples 4 and 5). The present inventors unexpectedly found that the anion exchange resin which has been considered difficult for industrially tabletting without adding water, particularly the non-crosslinked anion exchange resin represented by the formula (I), can provide industrially producible tablets by adding suitable amounts of both silicon dioxide and crystalline cellulose.

There is a known method of producing anion exchange resin tablets having excellent stability under humidity by adding water to suppress the hygroscopicity of anion exchange resin and lessening the rate in change of the diameters of base tablets caused by relative humidity, followed by further coating them with cellulose (Japanese Patent Application Laid-Open Publication Nos. 97330/95 and 157325/94). However, this prior art method is intended for use in coating of base tablets as cores containing a predetermined amount of water with a reduced change in the diameters of base tablets against humidity.

The base tablets of the present invention are prepared by tabletting anion exchange resin without adding water, particularly the non-crosslinked anion exchange resin represented by the formula (I), which is difficult for tabletting due to its strong hygroscopicity, and said known method of tabletting base tablets containing a predetermined amount of water was difficult to apply as such to the highly hygroscopic base tablets of the present invention.

The present inventors found that by coating the highly hygroscopic base tablets with a coating agent containing cellulose, it is possible to prevent not only the astringency of anion exchange resin, particularly the compound represented by the formula (I), but also the hygroscopicity of the base tablets to which water is not added, therefore, tablets having stability in long-term storage are provided.

Accordingly, the present invention also relates to coating tablets containing anion exchange resin, which comprises that base tablets are coated by coating agents containing celluloses and that the base tablets are provided by tabletting a mixture of the anion exchange resin added at least silicon dioxide and crystalline cellulose without adding water, and to a method for producing the same.

More specifically, the present invention relates to coating tablets containing non-crosslinked anion exchange resin prepared by adding at least silicon dioxide and crystalline cellulose to the non-crosslinked anion exchange resin represented by the formula (I):

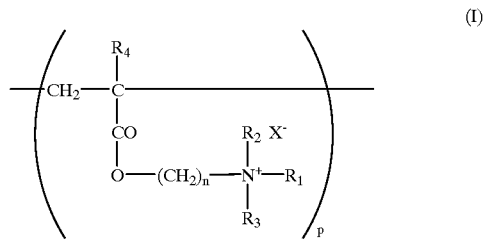

(wherein $R_1$ is an aralkyl group having from 7 to 10 carbon atoms or An alkyl group having from 1–20 carbon atoms; $R_2$ and $R_3$ are each independently the same or different and represent a lower alkyl group having from 1 to 4 carbon atoms; $R_4$ is a hydrogen atom or a lower alkyl group having 1 to 4 carbon atoms; X is a physiologically acceptable counter ion; n is an integer of from 1 to 3; and p is an average degree of polymerization of from 10 to 10,000) without adding water and tabletting the mixture to prepare tablets, followed by coating them with a coating agent containing celluloses and to a process for producing the same.

The preparation of the present invention is characterized in that manufacturing of the preparation with trace fillers, i.e. with a high content of drug, is made feasible. Further, the products by the present invention can be applied sufficiently to successive productions and to industrial productions.

The anion exchange resin of the present invention is preferably non-crosslinked anion exchange resin, more preferably the compound represented by the formula (I).

The substituent group $R_1$ in the compound represented by the formula (I) is an aralkyl group having from 7 to 10 carbon atoms or An alkyl group having from 1 to 20 carbon atoms, and the aryl group of said aralkyl group may have a substituent group but is preferably not substituted. More specifically, said alkyl group may be a straight chain or branched chain. Further more specifically, a benzyl group which may have a substituent group, phenylethyl group, methyl group, ethyl group, n-propyl group, iso-propyl group, hexyl group, dodecyl group, octadecyl group, eicosyl group and so on, more preferably a benzyl group, methyl group, hexyl group, dodecyl group, and octadecyl group can be listed as the examples.

The substituent groups $R_2$ and $R_3$ are each independently the same or different and may be a lower alkyl group having from 1–4 carbon atoms which may be a straight chain or branched chain. More specifically, a methyl group, ethyl group, n-propyl group, iso-propyl group, n-butyl group, iso-butyl group and so on, more preferably a methyl group can be listed as the examples.

The substituent group $R_4$ is a hydrogen atom or a lower alkyl group having from 1–4 carbon atoms which may be a straight chain or branched chain. More specifically, a hydrogen atom, methyl group, ethyl group, n-propyl group, iso-propyl group, n-butyl group, iso-butyl group and so on, more preferably a hydrogen atom or methyl group can be listed as the examples.

The counter ion X is particularly not limited insofar as it is a physiologically acceptable counter ion, and halogens, inorganic salts such as sulfate, carbonate and so on and organic acid salts such as acetate, propionate, malonate, ascorbate, glucuronate, glutamate, sulfonate, phosphate, preferably halogens, sulfate, phosphate, more preferably halogens such as chlorine ion, bromine ion and fluorine ion can be listed as the examples.

The compound shown as the formula (I) of the present invention can be produced by preparing its corresponding monomer, i.e. quaternary ammonium salt, and then polymerizing it in the presence of a polymerization initiator such as radical polymerization agent.

As the examples of the compound shown as the formula (I) of the present invention, the following compounds can be listed:
poly(acryloyloxyethyl-N,N,N-trimethylammonium chloride),
poly(methacryloyloxyethyl-N,N,N-trimethylammonium chloride),
poly(acryloyloxyethyl-N,N-dimethyl-N-benzylammonium chloride),
poly(methacryloyloxyethyl-N,N-dimethyl-N-benzylammonium chloride),
poly(acryloyloxyethyl-N,N-dimethyl-N-hexylammonium chloride),
poly(methacryloyloxyethyl-N,N-dimethyl-N-hexylammonium chloride),
poly(acryloyloxyethyl-N,N-dimethyl-N-dodecylammonium chloride),
poly(methacryloyloxyethyl-N,N-dimethyl-N-dodecylammonium chloride),
poly(acryloyloxyethyl-N,N-dimethyl-N-octylammonium chloride), and
poly(methacryloyloxyethyl-N,N-dimethyl-N-octylammonium chloride).

As a particularly preferable compound of said compound poly(acryloyloxyethyl-N,N-dimethyl-N-benzylammonium chloride) can be listed.

The content of the anion exchange resin of the present invention, particularly the compound shown as the formula (I), is in the range of from 50 to 95% by weight, preferably from 70 to 90% by weight, more preferably from 75 to 90% by weight, relative to the total weight of base tablets.

Silicon dioxide and crystalline cellulose used in the present invention are not particularly limited inasmuch as they are acceptable for uptaking peroral administration, preferably those having been used as peroral pharmaceutical preparations are industrially suitable.

Silicon dioxide is used to impart fluidity in the invention, and for example, hydrous silicon dioxide (also called white carbon), silicon dioxide (also called silica gel or silicic anhydride) and so on, preferably finely divided silicon dioxide and light silicic anhydride which are not hydrous, are used. The apparent specific gravity of silicon dioxide used is 70 g/l to 20 g/l, preferably 50 g/l to 20 g/l, and light silicic anhydride with lower apparent specific gravity is preferable. The adding content of silicon dioxide is 0.01 to 5% by weight, preferably 0.1 to 3% by weight, more preferably 0.1 to 1% by weight relative to the total weight of base tablets.

Crystalline cellulose is preferably fine crystalline cellulose, and the average particle diameter of crystalline cellulose is 5 to 50 microns, preferably 10 to 50 microns, more preferably 10 to 30 microns. The adding content of crystalline cellulose is 0.1 to 30% by weight, preferably 1 to 30% by weight, more preferably 10 to 30% by weight relative to the total weight of base tablets.

Silicon dioxide used in the present invention, particularly light silicic anhydride confers improvements on powder fluidity as its content increases and as the apparent specific gravity (bulk density) of silicon dioxide decreases, whereas tabletting properties (compressibility) seem to decrease. Therefore, if silicon dioxide is added in an amount of 5 parts or more relative to the compound of the formula (I), tabletting properties are lowered and cracks frequently occur in the resulting tablets.

Crystalline cellulose used in the present invention confers improvements on tabletting properties (compressibility) as its content increases and as the average particle size of crystalline cellulose decreases, whereas powder fluidity appears to be decreased. With respect to fine crystalline cellulose, if its content exceeds 30 parts, the scattering of the weights of tablets is raised. Because there is no particular advantage in using crystalline cellulose in a content of 30 parts or more relative to the compound of the formula (I), it is preferable to add inexpensive fillers such as lactose if a large amount of additional fillers are required.

Accordingly, the present invention relates more specifically to tablets containing anion exchange resin prepared by tabletting a water-free mixture containing at least anion exchange resin, preferably the non-crosslinked anion exchange resin represented by the formula (I), light silicic anhydride with a low apparent specific gravity of 70 g/l to 20 g/l, preferably 50 g/l to 20 g/l, and crystalline cellulose with an average particle diameter of 50 to 10 microns, preferably 30 to 10 microns, as well as to a process for producing the same.

More specifically, the present invention relates to tablets prepared by tabletting a water-free mixture containing at least the non-crosslinked anion exchange resin represented by the formula (I), silicic anhydride with a low apparent specific gravity of 50 g/l to 20 g/l, preferably 40 g/l to 20 g/l, and crystalline cellulose with an average particle diameter of 50 to 10 microns, preferably 30 to 10 microns wherein the content of said anion exchange resin is 50 to 90% by weight, preferably 70 to 90% by weight, more preferably 75 to 90% by weight relative to the total weight of tablets, as well as to a process for producing the same.

Further, the present invention relates to coating agents containing non-crosslinked anion exchange resin prepared by further coating said tablets with a coating agent containing cellulose, and to a process for producing the same.

Besides said silicon dioxide and crystalline cellulose, ingredients conventionally used in tabletting can be added in such a range as not to hinder the object of the present invention to the tablets before coating which serve as the base tablets of the present invention. For example, the following can be added as necessary;

fillers such as disaccharides or monosaccharides such as lactose (milk sugar), sucrose, glucose, mannitol, sorbitol and so on, starch such as potato starch, wheat starch, corn starch, rice starch, inorganic substances such as calcium phosphate and calcium sulfate, higher fatty acids and metallic salts thereof (e.g. stearic acid, magnesium stearate and so on), lubricants such as higher alcohol, talk, synthetic aluminum silicate and so on, disintegrators such as starch, sodium salts or potassium salts of carboxymethyl cellulose, methyl cellulose, carboxymethyl starch, sodium alginate and so on, binders such as starch, sucrose, gelatin, gum Arabic, methyl cellulose, carboxymethyl cellulose sodium, polyvinyl pyrrolidone, polymethyl pyrrolidone and so on.

The tablets before coating, which serve as the base tablets of the present invention, can be produced by mixing the respective ingredients and tabletting the mixture. The order of addition of the respective ingredients is not particularly limited, but preferably crystalline cellulose and silicon dioxide are mixed, and then the compound represented by the formula (I) is preferably gradually added and mixed, and other components are added and mixed as necessary to the mixture.

The mallet pressure for tabletting is not particularly limited, preferably 2 tons or less.

The celluloses contained in the coating agent used in the coating step of the present invention is not particularly limited inasmuch as it is pH independent and water-soluble. Specific examples are hydroxypropyl cellulose, hydroxypropyl methyl cellulose, methyl cellulose and so on, among which hydroxypropyl methyl cellulose is preferable.

In the present invention, these of celluloses may be used each solely, or, as necessary, a small amount of wax, titanium oxide, talk, low substituted hydroxypropyl cellulose, polyethylene glycol, triethyl citrate and soon can also be added to the celluloses for use. For strength and from an economical viewpoint of the resulting coating film, polyethylene glycol (Macrogol) is preferably added.

The amount of cellulose coated is too large if the concentration of cellulose in the coating solution is high, so its use at high concentration is not preferable, and its concentration is preferably less than 20% by weight, more preferably about 6 to 15% by weight. If polyethylene glycol (Macrogol) is to be added, its concentration is preferably about 1 to 50% by weight, more preferably about 5 to 40% by weight.

As other coating agents, acid-soluble coating agents can be used. For example, it is possible to use coating agents dissolving in gastric acid, such as diethyl aminomethacrylate, polyvinyl acetal diethyl aminoacetate (AEA), dimethyl aminoethyl methacrylate-methyl methacrylate copolymer (trade name: Eudragit E (methyl methacrylate-butyl methacrylatedimethyl aminoethyl methacrylate copolymer)), cellulose acetate N,N-di-n-butylhydroxypropyl ether (CABP) and so on.

The method of coating is not particularly limited, but spray coating is preferable.

Preferably, the amount of the coating is such that the coating film itself is coated in an amount of 1 to 10% by weight relative to the tablets (base tablets). For the purpose of masking of astringency, its effect can be achieved in an amount of 1% by weight or more, but there is no particular usefulness even if 10% by weight or more coating is applied, and about 3% by weight coating is most preferable. For coating, the water content of base tablets is measured and the step of coating is continued until there is no increase in water content.

Hereinafter, the present invention is described in more detail with reference to Examples, but it is evident that the invention is not limited to the following examples insofar as the scope of the invention lies in the gist thereof.

EXAMPLE 1

(1) Mixing Step

The following mixing apparatus was used for mixing each ingredient.

Mixing apparatus: POWREX V-type mixing machine FMV100

(1-1) Mixing method 1000 g of crystalline cellulose and 50 g of light silicic anhydride shown in the mixture formulation below were weighted, introduced into the mixing machine and mixed for 5 minutes.

The total amount of poly(acryloyloxyethyl-N,N-dimethyl-N-benzylammonium chloride) (the compound (referred to hereinafter as "Compound 1") of the formula (I) wherein $R_1$ is a benzyl group, $R_2$ and $R_3$ are methyl groups, $R_4$ is a hydrogen atom, n is 2, and X is a chlorine ion) was divided into 4 portions and each portion was added to said mixture at 5-minute intervals and mixed in it.

Thereafter, 50 g of magnesium stearate was weighed and introduced into the mixing machine and mixed for 1 minute.

| (1-2) Mixture formulation (10 kg) | |
|---|---|
| Compound 1 | 8900 g |
| crystalline cellulose (trade name: Abicel PH-F20 (average particle diameter: 17 microns)) | 1000 g |
| magnesium stearate | 50 g |
| light silicic anhydride (apparent specific gravity (bulk density) 30 g/l) | 50 g |

(2) Tabletting Step

The following tabletting apparatus was used in the tabletting step.

Tabletting apparatus: Rotary type tabletting machine HT-AP15SS (Hata Tekkosho Co.)

| (2-1) Tabletting conditions | |
|---|---|
| Rotation | 35 rpm |
| Thickness | 5 mm |
| Hardness | 7 or more |
| upper and lower mallet pressure | 2 tons or less |
| Forced feeder | used |

(3) Coating Step

The following coating machine was used in the coating step.

Coating machine: Doria coater 650 (POWREX)

(3-1) Coating method 7 kg of the tablets obtained in (2) above are introduced into a pan, and the coating pan is set at a 0 rpm at a suction air temperature of 80° C., and it is left until its exhaust temperature becomes constant. At this time, it is confirmed that the exhaust temperature is 50° C. or more. 20 tablets are taken and weighed, and then divided into powder, and its water content is determined. The number of revolutions is set at 7 rpm, and it is initiated to spray a coating liquid with the formulation shown below at 12 g/min. 30 minutes later, the number of revolutions is set at 15 rpm and spraying is conducted at about 18 g/min. 20 tablets are sampled and measured for the weight and water content of the tablets at suitable intervals. When the water content does not increase any more and the weight of tablets becomes 3% relative to the base tablets, spraying is terminated and the number of revolutions is set at 5 rpm and the tablets are dried for about 60 minutes.

| (3-2) Formulation of the coating liquid | |
|---|---|
| Hydroxypropyl methyl cellulose 2910 | 400 g |
| Macrogol 6000 | 120 g |
| Ion-exchanged water | 4600 g |

EXAMPLE 2

(1) Mixing Step

The following mixing apparatus was used for mixing each ingredient.

Mixing apparatus: POWREX V-type mixing machine FMV100

(1-1) Mixing method 2000 g of crystalline cellulose and 50 g of light silicic anhydride shown in the mixture formulation below are weighted, introduced into the mixing machine and mixed for 5 minutes.

The total amount of Compound 1 is divided into 4 portions and each portion is added to said mixture at 5-minute intervals and mixed in it.

Thereafter, 50 g of magnesium stearate is weighed and introduced into the mixing machine and mixed for 1 minute.

| (1-2) Mixture formulation (10 kg) | |
|---|---|
| Compound 1 | 7900 g |
| crystalline cellulose (trade name: Abicel PH-301 (average particle diameter: 40 microns)) | 2000 g |
| magnesium stearate | 50 g |
| light silicic anhydride (apparent specific gravity (bulk density) 50 g/l) | 50 g |

(2) Tabletting Step, Coating Step

The tabletting step and coating step were carried out in the same manner as in Example 1.

EXAMPLE 3

(1) Mixing Step

The following mixing apparatus was used for mixing each ingredient.

Mixing apparatus: POWREX V-type mixing machine FMV100

(1-1) Mixing method 1000 g of crystalline cellulose, 550 g of milk sugar, and 50 g of light silicic anhydride shown in the mixture formulation below are weighted, introduced into the mixing machine and mixed for 5 minutes.

The total amount of Compound 1 is divided into 4 portions and each portion is added to said mixture at 5-minute intervals and mixed in it.

Thereafter, 50 g of magnesium stearate is weighed and introduced into the mixing machine and mixed for 1 minute.

| (1-2) Mixture formulation (10 kg) | |
|---|---|
| Compound 1 | 8350 g |
| crystalline cellulose (trade name: Abicel PH-F20 (average particle diameter: 17 microns)) | 1000 g |
| milk sugar | 550 g |
| magnesium stearate | 50 g |
| light silicic anhydride (apparent specific gravity (bulk density) 50 g/l) | 50 g |

(2) Tabletting Step, Coating Step

The tabletting step and coating step were carried out in the same manner as in Example 1.

EXAMPLE 4

(1) Mixing Step, Tabletting Step

The mixing step and tabletting step were carried out in the same manner as in Example 1.

(2) Coating Step (2-1) Coating method

The coating method is carried out in the same manner as in Example 1 until the step of drying, and 5 g of carnauba wax is further added, and the number of revolutions is set at 5 rpm and the machine is operated for 5 minutes.

| (2-2) Formulation of the coating liquid | |
|---|---|
| Hydroxypropyl methyl cellulose 2910 | 400 g |
| Macrogol 6000 | 120 g |
| Titanium oxide | 28 g |
| Ion-exchanged water | 4000 g |
| (2-3) Lubricant | |
| Powder carnauba wax | 5 g |

COMPARATIVE EXAMPLE 1

(1) Mixing Step

The following mixing apparatus was used for mixing each ingredient.

Mixing apparatus: POWREX V-type mixing machine FMV100

(1-1) Mixing method 1000 g of crystalline cellulose and 50 g of light silicic anhydride shown in the mixture formulation below are weighted, introduced into the mixing machine and mixed for 5 minutes.

The total amount of Compound 1 is divided into 4 portions and each portion is added to said mixture at 5-minute intervals and mixed in it.

Thereafter, 50 g of magnesium stearate is weighed and introduced into the mixing machine and mixed for 1 minute.

Because it was difficult to mix Compound 1 with water, 890 g water was added by spraying.

| (1-2) Mixture formulation (10 kg) | |
|---|---|
| Compound 1 | 8010 g |
| water | 890 g |
| crystalline cellulose (trade name: Abicel PH-F20 (average particle diameter: 17 microns) | 1000 g |
| magnesium stearate | 50 g |

-continued

| (1-2) Mixture formulation (10 kg) | |
|---|---|
| light silicic anhydride (apparent specific gravity (bulk density) 30 g/l) | 50 g |

COMPARATIVE EXAMPLE 2

(1) Mixing Step

The following mixing apparatus was used for mixing each ingredient.

Mixing apparatus: POWREX v-type mixing machine FMV100

(1-1) Mixing method 1000 g of crystalline cellulose and 50 g of light silicic anhydride shown in the mixture formulation below are weighted, introduced into the mixing machine and mixed for 5 minutes.

The total amount of Compound 1 is divided into 4 portions and each portion is added to said mixture at 5-minute intervals and mixed in it.

Thereafter, 50 g of magnesium stearate is weighed and introduced into the mixing machine and mixed for 1 minute.

| (1-2) Mixture formulation (10 kg) | |
|---|---|
| Compound 1 | 8900 g |
| crystalline cellulose (trade name: Abicel PH-301 (average particle diameter: 40 microns) | 1000 g |
| magnesium stearate | 50 g |
| light silicic anhydride (apparent specific gravity (bulk density) 30 g/l) | 50 g |

(2) Tabletting Step, Coating Step

The tabletting step and coating step were carried out in the same manner as in Example 1.

COMPARATIVE EXAMPLE 3

(1) Mixing Step

The following mixing apparatus was used for mixing each ingredient.

Mixing apparatus: POWREX V-type mixing machine FMV100

(1-1) Mixing method 1000 g of crystalline cellulose and 50 g of light silicic anhydride shown in the mixing formulation below are weighted, introduced into the mixing machine and mixed for 5 minutes.

The total amount of Compound 1 is divided into 4 portions and each portion is added to said mixture at 5-minute intervals and mixed in it.

Thereafter, 50 g of magnesium stearate is weighed and introduced into the mixing machine and mixed for 1 minute.

| (1-2) Mixture formulation (10 kg) | |
|---|---|
| Compound 1 | 8900 g |
| crystalline cellulose (trade name: Abicel PH-302 (average particle diameter: 120 microns) | 1000 g |
| magnesium stearate | 50 g |
| light silicic anhydride (apparent specific gravity (bulk density) 30 g/l) | 50 g |

(2) Tabletting Step, Coating Step

The tabletting step and coating step were carried out in the same manner as in Example 1.

COMPARATIVE EXAMPLE 4

(1) Mixing Step

The following mixing apparatus was used for mixing each ingredient.

Mixing apparatus: POWREX V-type mixing machine FMV100

(1-1) Mixing method 50 g of light silicilic anhydride in the mixture formulation below is weighed and introduced into the mixing machine.

The total amount of Compound 1 is divided into 4 portions and each portion is added to it at 5-minute intervals and mixed in it.

Thereafter, 50 g of magnesium stearate is weighed and introduced into the mixing machine and mixed for 1 minute.

| (1-2) Mixture formulation (10 kg) | |
|---|---|
| Compound 1 | 9900 g |
| magnesium stearate | 50 g |
| light silicic anhydride (apparent specific gravity (bulk density) 30 g/l) | 50 g |

(2) Tabletting Step, Coating Step

The tabletting step and coating step were carried out in the same manner as in Example 1.

COMPARATIVE EXAMPLE 5

(1) Mixing Step

The following mixing apparatus was used for mixing each ingredient.

Mixing apparatus: POWREX V-type mixing machine FMV100

(1-1) Mixing method 1000 g of crystalline cellulose in the mixture formulation below is weighted and introduced into the mixing machine.

The total amount of Compound 1 is divided into 4 portions and each portion is added to said mixture at 5-minute intervals and mixed in it.

Thereafter, 50 g of magnesium stearate is weighed and introduced into the mixing machine and mixed for 1 minute.

| (1-2) Mixture formulation (10 kg) | |
|---|---|
| Compound 1 | 8950 g |
| crystalline cellulose (trade name: Abicel PH-F20 (average particle diameter: 17 microns) | 1000 g |
| magnesium stearate | 50 g |

(2) Tabletting Step, Coating Step

The tabletting step and coating step were carried out in the same manner as in Example 1.

COMPARATIVE EXAMPLE 6

(1) Mixing Step

The following mixing apparatus was used for mixing each ingredient.

Mixing apparatus: POWREX V-type mixing machine FMV100

(1-1) Mixing method 9950 g of Compound 1 and 50 g of magnesium stearate shown in the mixture formulation below are weighted, introduced into the mixing machine and mixed for 1 minute.

| (1-2) Mixture formulation (10 kg) | |
|---|---|
| Compound 1 | 9950 g |
| magnesium stearate | 50 g |

(2) Tabletting Step, Coating Step

The tabletting step and coating step were carried out in the same manner as in Example 1.

COMPARATIVE EXAMPLE 7

Tablets prepared in only the tabletting step in Example 1 without the coating step.

TEST EXAMPLE 1

In tablets obtained under a tabletting pressure of 2 tons or less, powder fluidity due to scattering of the weights of base tablets was indicated in the frequency of occurrence of fracture and cracking in coating. The present article showed compressibility in this appearance test because it is highly hygroscopic to increase its weight during a wearing test.

The test results are shown in Table 1.

TABLE 1

| | Scattering in weights of base tablets | Fracture & cracking | Tabletting properties |
|---|---|---|---|
| Example 1 | Small | None | ⊙ |
| Example 2 | Small | None | ⊙ |
| Example 3 | Small | None | ⊙ |
| Com. Ex. 1 | unable to tablet | — | — |
| Com. Ex. 2 | Small | cracks on surface | Δ |
| Com. Ex. 3 | Small | cracks on surface, fracture at edge | Δ |
| Com. Ex. 4 | Small | cracks on surface, fracture at edge | Δ |
| Com. Ex. 5 | Middle | None | ○ |
| Com. Ex. 6 | Large | cracks on surface, fracture at edge | X |

Comparative Example 1 to which water was added could not be sufficiently mixed because of its deliquescence and stringing caused by water, and even its tabletting was unable.

In the preparations without using water, tabletting and coating were able in any examples and comparative examples, and tablets free of problems with powder fluidity and compressibility were obtained in Examples 1, 2 and 3.

A formulation to which crystalline cellulose is not added is shown in Comparative Example 4, a formulation to which light silicic anhydride is not added is shown in Comparative Example 5, and a formulation to which both of them are not added is shown in Comparative Example 6. If crystalline cellulose is not added, tabletting properties (compressibility) are significantly deteriorated, and cracks appear on the surfaces of tablets. In the formulation to which light silicic anhydride is not added, powder fluidity is lowered and scattering in the weights of tablets is very high. When both of them are not added, scattering in the weights of tablets is extremely high, while there are many cracks and fracture, and tabletting properties are poor.

In addition, a formulation to which crystalline cellulose with an average particle diameter of 40 microns is added is shown in Comparative Example 2, and a formulation to which crystalline cellulose with an average particle diameter of 120 microns is added is shown in Comparative Example 3, and both of them were examples where light silicic anhydride with an apparent specific gravity (bulk density) 30 g/l was used. These comparative examples show that even if the average particle diameter of crystalline cellulose added is larger, tabletting is made feasible by adding light silicic anhydride with low apparent specific gravity (bulk density) (Example 2), but if light silicic anhydride with large apparent specific gravity (bulk density) is added, cracking and fracture frequently occur while tabletting properties are made poor.

Further, tablets with a high drug content can be produced by use of light silicic anhydride with low apparent density (bulk density) and crystalline cellulose with low average particle diameter as shown in Example 1, thus contributing to a reduction in the dosage of the pharmaceutical preparation. The formulation of the tablets according to the present invention enables stable and direct tabletting using only the mixing step without any granulation step, to sufficiently cope with successive production.

TEST EXAMPLE 1

The present tablets are deformed when the water content exceeds 7%, and they deliquesce upon further absorption of water The increase in stability by coating was compared in terms of deformation after storage at 60° C. under a relative humidity of 90% for 20 minutes. The astringency of the tablets when placed for 30 seconds in the mouth was also compared.

The results of the test are shown in Table 2.

TABLE 2

| | Deformation | Astringency |
|---|---|---|
| Example 1 | absent | absent |
| Example 4 | absent | absent |
| Com. Ex. 7 | present | present |

It is understood that by coating, the stability of tablets is increased and their stringency is masked, so easily administered tablets are obtained.

INDUSTRIAL APPLICABILITY

As described above, the pharmaceutical composition and tablets of the present invention have the great advantages that they are superior in dosage and administration methods to peroral cholesterol depressants containing conventional anion exchange resin, and further that even at the time of manufacturing, no granulation step is required. Further, by coating the resulting tablets with cellulose, it is possible to obtain tablets easily administered without any stringency of the drug.

We claim:

1. A pharmaceutical composition comprising a tablet obtainable by admixing in the absence of water, silicon dioxide, crystalline cellulose, a pharmaceutically acceptable carrier, and a non-crosslinked anion exchange resin represented by the formula (I):

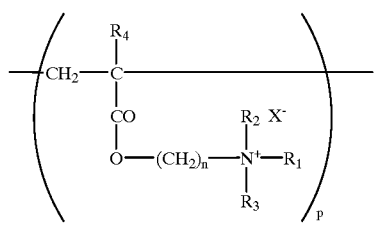

wherein $R_1$ is an aralkyl group having from 7 to 10 carbon atoms or an alkyl group having from 1–20 carbon atoms; $R_2$ and $R_3$ are each independently the same or different and represent a lower alkyl group having from 1–4 carbon atoms; $R_4$ is a hydrogen or a lower alkyl group having from 1–4 carbon atoms; X is a physiologically acceptable counter ion; n is an integer of from 1 to 3; and p is an average degree of polymerization of from 10 to 10,000, wherein said silicon dioxide is present in an amount of 0.01 to 5% by weight relative to the total weight of base tablet and wherein said crystalline cellulose is present in the amount of 0.1 to 30% by weight relative to the total weight of the base tablet.

2. The pharmaceutical composition of claim 1 wherein the anion exchange resin is poly(acryloxyethyl-N,N-dimethyl-N'benzylammonium chloride).

3. The pharmaceutical composition of claim 1 wherein the silicon dioxide is present in an amount of 0.1 to 5% by weight of the tablet.

4. The pharmaceutical composition of claim 1 wherein the crystalline cellulose is present in an amount of about 1 to 30% by weight of the tablet.

5. The pharmaceutical composition of claim 1 wherein the apparent specific gravity of the silicon dioxide is 70 g/l to 20 g/l, and the average particle diameter of crystalline cellulose is 50 to 10 microns.

6. The pharmaceutical composition of claim 1 wherein the tablet is coated with an agent containing cellulose.

7. The pharmaceutical composition of claim 6 wherein the cellulose is hydroxypropyl methyl cellulose.

8. A pharmaceutical tablet obtained by admixing in the absence of water, silicon dioxide, crystalline cellulose, a pharmaceutically acceptable carrier, and a non-crosslinked anion exchange resin represented by formula (I):

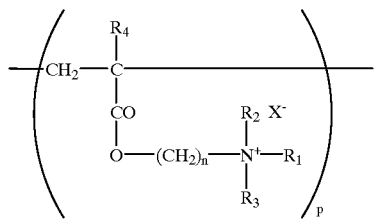

wherein $R_1$ is an aralkyl group having from 7 to 10 carbon atoms or an alkyl group having from 1–20 carbon atoms; $R_2$ and $R_3$ are each independently the same or different and represent a lower alkyl group having from 1–4 carbon atoms; $R_4$ is a hydrogen or a lower alkyl group having from 1–4 carbon atoms; X is a physiologically acceptable counter ion; n is an integer of from 1 to 3; and p is an average degree of polymerization of from 10 to 10,000, and forming a tablet from the admixture, wherein said silicon dioxide is present in an amount of 0.01 to 5% by weight relative to the total weight of base tablet and wherein said crystalline cellulose is present in the amount of 0.1 to 30% by weight relative to the total weight of the base tablet.

9. A pharmaceutical tablet of claim 8 wherein the anion exchange resin is poly(acryloxyethyl-N,N-dimethyl-N'benzylammonium chloride).

10. A pharmaceutical tablet of claim 8 wherein the silicon dioxide is present in an amount of 0.1 to 5% by weight of the tablet, and the crystalline cellulose is present in an amount of about 1 to 30% by weight of the tablet.

11. A pharmaceutical tablet of claim 8 wherein the apparent specific gravity of the silicon dioxide is 70 g/l to 20 g/l, and the average particle diameter of crystalline cellulose is 50 to 10 microns.

12. A pharmaceutical tablet of claim 8 further comprising coating the tablet with an agent containing cellulose.

13. A method for producing a pharmaceutical composition comprising a tablet, the method comprising:

(a) admixing in the absence of water, silicon dioxide, crystalline cellulose, a pharmaceutically acceptable carrier, and a non-crosslinked anion exchange resin represented by formula (I):

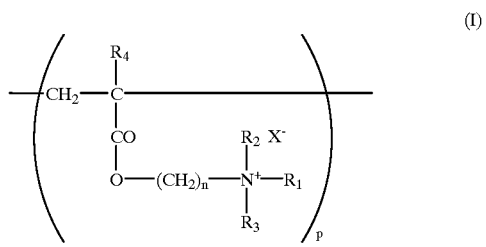

wherein $R_1$ is an aralkyl group having from 7 to 10 carbon atoms or an alkyl group having from 1–20 carbon atoms; $R_2$ and $R_3$ are each independently the same or different and represent a lower alkyl group having from 1–4 carbon atoms; $R_4$ is a hydrogen or a lower alkyl group having from 1–4 carbon atoms; X is a physiologically acceptable counter ion; n is an integer of from 1 to 3; and p is an average degree of polymerization of from 10 to 10,000, and (b) forming a tablet from the admixture, wherein said silicon dioxide is present in an amount of 0.01 to 5% by weight relative to the total weight of base tablet and wherein said crystalline cellulose is present in the amount of 0.1 to 30% by weight relative to the total weight of the base tablet.

14. The method of claim 13 wherein the anion exchange resin is poly(acryloxyethyl-N,N-dimethyl-N'benzylammonium chloride).

15. The method of claim 13 wherein the silicon dioxide is present in an amount of 0.1 to 5% by weight of formed the tablet, and the crystalline cellulose is present in an amount of about 1 to 30% by weight of the formed tablet.

16. The method of claim 13 wherein the apparent specific gravity of the silicon dioxide is 70 g/l to 20 g/l, and the average particle diameter of crystalline cellulose is 50 to 10 microns.

17. The method of claim 13 further comprising coating the tablet with an agent containing cellulose.

* * * * *